(12) United States Patent
Aharon et al.

(10) Patent No.: US 10,912,611 B2
(45) Date of Patent: Feb. 9, 2021

(54) AUTOMATIC AESTHETIC TREATMENT DEVICE AND METHOD

(71) Applicant: S & Y Enterprises LLC, West Orange, NJ (US)

(72) Inventors: Oren Aharon, Haifa (IL); Yehuda Poran, Kibbutz Elrom—Golan Heights (IL)

(73) Assignee: S & Y ENTERPRISES LLC, West Orange, NJ (US)

( * ) Notice: Subject to any disclaimer, the term of this patent is extended or adjusted under 35 U.S.C. 154(b) by 861 days.

(21) Appl. No.: 15/012,371

(22) Filed: Feb. 1, 2016

(65) Prior Publication Data

US 2017/0215962 A1 Aug. 3, 2017

(51) Int. Cl.
| *A61B 18/20* | (2006.01) |
| *A61N 5/06* | (2006.01) |
| *A61B 90/00* | (2016.01) |
| *A61N 5/067* | (2006.01) |
| *A61B 18/00* | (2006.01) |

(52) U.S. Cl.
CPC .......... *A61B 18/203* (2013.01); *A61B 90/361* (2016.02); *A61N 5/0616* (2013.01); *A61B 2018/0047* (2013.01); *A61B 2018/00476* (2013.01); *A61B 2018/00982* (2013.01); *A61B 2018/2035* (2013.01); *A61B 2018/2065* (2013.01); *A61B 2018/20359* (2017.05); *A61B 2090/367* (2016.02); *A61B 2090/3616* (2016.02); *A61N 2005/067* (2013.01); *A61N 2005/0644* (2013.01); *A61N 2005/0651* (2013.01); *A61N 2005/0659* (2013.01); *A61N 2005/0666* (2013.01)

(58) Field of Classification Search
CPC ............ A61B 18/20; A61F 9/008; A61N 5/06
USPC ........................................................ 606/2–19
See application file for complete search history.

(56) References Cited

U.S. PATENT DOCUMENTS

| 4,648,892 A | * | 3/1987 | Kittrell ................... A61B 17/22 600/342 |
| 6,110,165 A | * | 8/2000 | Ota ......................... A61F 9/008 606/11 |
| 6,575,963 B1 | * | 6/2003 | Van Saarloos ..... G02B 26/0875 606/10 |
| 2006/0206103 A1 | * | 9/2006 | Altshuler ............. A61B 18/203 606/9 |
| 2007/0106285 A1 | * | 5/2007 | Raksi ...................... A61F 9/008 606/17 |
| 2009/0054880 A1 | | 2/2009 | Aharon ............................ 606/9 |

(Continued)

*Primary Examiner* — Lynsey C Eiseman
(74) *Attorney, Agent, or Firm* — Stein IP, LLC

(57) ABSTRACT

An aesthetic treatment device uses multiple light sources, lasers or LEDs focused on the treatment area from different directions. The multiple light sources for treatment purposes could have the same wavelength or different wavelengths each optimized for a different application. Target selection is performed by a dual wavelength smart illumination system combined with an imaging system, a smart processor for target recognition and a scanning system that directs the focused light from laser sources to an automatically selected treatment area. A motorized optical system performs a dual role of: focusing the laser sources and also steering the focused light to specific locations as designated by the imaging and processing systems.

2 Claims, 16 Drawing Sheets

(56) References Cited

U.S. PATENT DOCUMENTS

| | | | |
|---|---|---|---|
| 2009/0259218 A1* | 10/2009 | Bitter | A61B 18/203 606/9 |
| 2013/0345685 A1 | 12/2013 | Poran et al. | 606/9 |
| 2014/0107635 A1* | 4/2014 | Poran | A61B 18/203 606/9 |

* cited by examiner

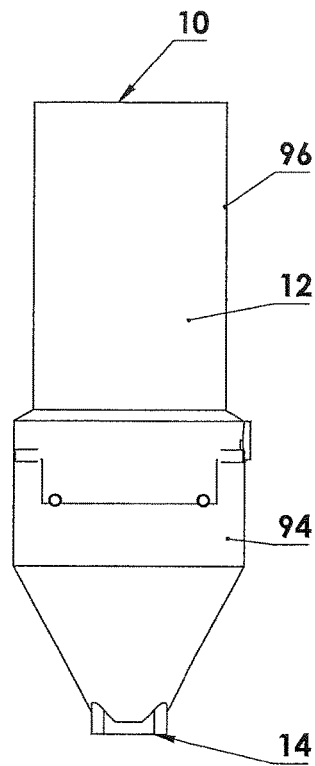
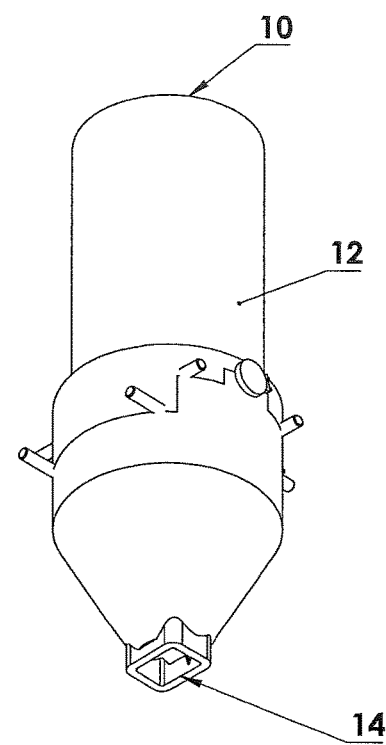
FIG 1
FIG 2
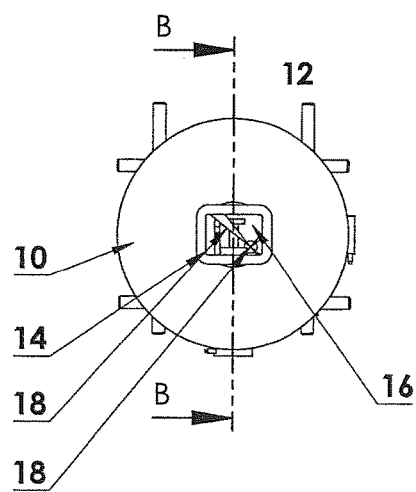
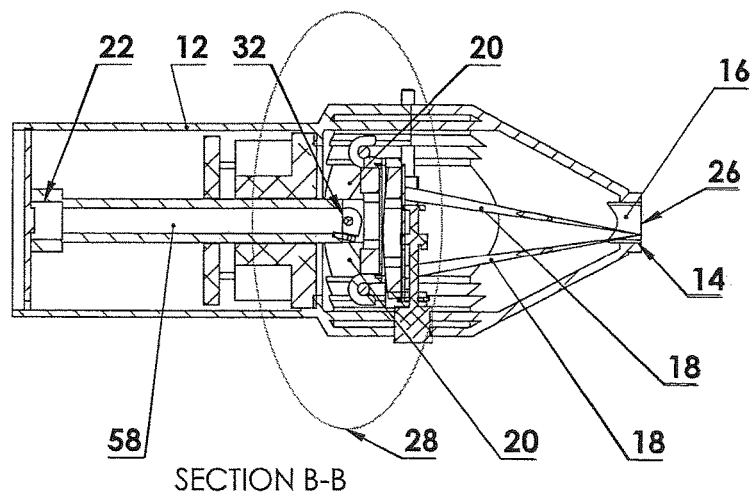
SECTION B-B
FIG 3
FIG 4

BLOCK DIAGRAM

AUTOMATIC AESTHETIC TREATMENT DEVICE AND METHOD

BACKGROUND OF THE INVENTION

1. Field of the Invention

Aspects of the invention relate to a miniature device which performs aesthetic treatments such as acne treatment, wrinkle removal, hair removal, rejuvenation and other applications based on light treatment. The system may comprise a detection system which evaluates the exact area to be treated and a multiple wavelength laser or LED sources tuned to optimally treat the unwanted aesthetic, an imaging device for discerning the targets to be treated, a computer device, such as a processor, with algorithms for automatic target recognition and a motorized dual axis device for automatically aiming the light sources' focal point(s) to the selected areas.

2. Description of the Related Art

In known aesthetic treatment devices, treatment is performed by flooding a relatively large area of skin with light without differentiation between healthy skin and the area to be treated. A typical system for dermatological treatment is described in U.S. Patent Publication No. 2009/0054880 A1, inventor Oren Aharon, intended to perform dermatological treatment by intense pulses of light radiated over large skin areas. The treatment selection is performed by chromatic characteristics of the skin or hair follicles and selection between treated and not to be treated areas is performed by the light source wavelength selection in a process called photo thermolysis or wavelength depended light absorption.

Light is absorbed by dark objects, so laser energy can be absorbed by dark material in the skin, but with higher speed and intensity. This dark target matter, or chromospheres, can be naturally-occurring or artificially introduced.

SUMMARY OF THE INVENTION

Recently, a new device designed by the same inventors as the present application, U.S. Patent Pub. No. 2013-0345685-A1, was disclosed such that a special illumination technique capitalizes on oblique illumination, thereby enhancing the image contrast. This contrast enhancement technology in conjunction with a high end imaging device allows an image quality high enough to be automatically processed for determining the areas for treatment. An aspect of the present invention may incorporate the multi-illumination system disclosed in U.S. Patent Pub. No. 2013-0345685, but in another aspect, such a multi-illumination system is not utilized.

According to an aspect of the present invention, the treating source will comprise a laser or an LED, or a system of lasers or LEDS, each with an appropriate wavelength dedicated to a specific treatment application. Preferably, each light source will be a dual wavelength laser capable of performing treatment by being transmitted through the skin or by local skin penetration. The system's laser power is focused and directed to treatment areas by two XY motors, such that upon homing in on the target, the system automatically fires the light sources with enough energy to perform the treatment.

According to an aspect of the present aesthetic treatment device, an aesthetic treatment device has a combination and optical design where the focusing laser optics is also a component for beam direction to selected areas of the skin for treatment.

According to one aspect of the present aesthetic treatment device, this device achieves and sometimes overcomes the performance of the systems existing in the market for the above procedures, while integrating all the capabilities of aesthetic treatment in a miniature hand held automatic treatment apparatus. For treatment, according to one aspect, the apparatus is based on multiple light sources, lasers or LEDs focused on the treatment area from different directions. The multiple light sources for treatment purposes could have the same wavelength or different wavelengths each optimized for a different application. Target selection is performed by a dual wavelength smart illumination system combined with an imaging system or just the imaging system, a smart processor for target recognition and a scanning system that directs the focused light from laser sources to an automatically selected treatment area. A motorized optical system performs a dual role of: focusing the laser sources and also steering the focused light to specific locations as designated by the imaging and processing systems.

Due to the above features, the aesthetic treatment device according to an aspect is potentially usable for all hair types, tattoo removal and other types of aesthetic systems with automatic treatment modes.

According to an aspect, the aesthetic treatment device can be upgraded so that the automatic system is capable of treating even larger areas by adding a dual axis mirror scanning system.

In addition, by coupling together several automatic scanning treatment devices, even larger areas could be treated simultaneously.

Furthermore, an even larger area could be simultaneously treated by using a scanning mirror to scan, across a patient's skin, multiple treatment devices which are coupled together.

Many disadvantages of prior art aesthetic treatment devices are advantageously solved by aspects of the present invention. A partial list is as follows:

In prior art systems, the user has to recognize and direct the laser to a specific area, which is tedious and may be tiring.

Some prior art lenses for laser focusing and mirrors for scanning are expensive and increase the device's overall dimensions, wherein, according to an aspect, the present aesthetic treatment device can use the same lens for focusing and also for beam steering.

Moreover, for improved operation, the focusing is performed by two perpendicular cylindrical lenses each independently activated by a respective linear scanning motor, greatly simplifying the mechanical and motors' control, while the irradiated focal point is kept in focus across the skin.

According to an aspect, a mechanical guidance system comprises a curved lens mounted on a dual axis motorized follicle spherical system, to focus and automatically operate the aesthetic treatment device in near spherical movements.

According to an aspect, the mechanical guidance system comprises two independently motorized cylindrical lenses to focus the lasers at a point below the skin surface along two perpendicular directions. Motors to move the lenses in perpendicular directions yield XY scanning of the focused beam across a skin surface.

According to an aspect, several aesthetic automatic treatment devices are coupled together to further increase the treatment area and are scanned across the skin surface by an additional mirror.

According to an aspect, the aesthetic treatment device is further coupled to a dual axis mirror scanner to still further increase the treatment area of the skin surface.

According to another aspect, there is a seek and treat aesthetic device comprising: a treatment aperture to be placed on a skin area to be treated; multiple treatment laser modules having wavelengths in the IR region from 670 nm to 1000 nm mounted on an optical bench circumference and focused to a treatment area; a first cylindrical lens focusing the laser modules in a direction according to its optical power and along its optical axis; a second cylindrical lens perpendicular to the first cylindrical lens, focusing the laser modules in the perpendicular direction to the first cylindrical lens; first and second motorized linear stages to respectively scan the first and second cylindrical lenses in perpendicular directions; an imaging device, sensitive to the illumination system, to discern features on or under the skin within the predetermined area of skin to be treated; a processor to perform an algorithm to recognize a target to be treated within the predetermined skin area and to direct the focused laser modules towards the target; an electronic driver to activate liner motorized stages to aim laser focused beams toward the target to be treated; and a computerized controller to guide and perform the seek and treat procedure automatically by independently moving the two perpendicular linear stages and aiming to the target to be treated.

According to an aspect, the seek and treat aesthetic device immediately above, the imaging device takes two images of the treatment aperture from two different locations; and the algorithm creates a 3D image of skin surface from two images and selects features protruding above the skin area as the target to be treated.

According to another aspect of the seek and treat aesthetic device above, the imaging device takes two images of the treatment aperture from two different locations; with one of the cylindrical lenses being equipped on its curved side with two prismatic elements that when shifted in front of an aperture of a camera, shifts the location of an observation point of the skin area being viewed from a first of the two different locations to a second of the two different locations.

Additional aspects and/or advantages of the invention will be set forth in part in the description which follows and, in part, will be obvious from the description, or may be learned by practice of the invention.

BRIEF DESCRIPTION OF DRAWINGS

These and/or other aspects and advantages of the invention will become apparent and more readily appreciated from the following description of the embodiments, taken in conjunction with the accompanying drawings of which:

FIG. 1 is a side outside view of an assembled aesthetic treatment device according to an aspect;

FIG. 2 is a side perspective view of the aesthetic treatment device shown in FIG. 1;

FIG. 3 is a front end view of the aesthetic treatment device shown in FIG. 1;

FIG. 3 is a view of the outer surface of the aesthetic treatment device shown in FIG. 1;

FIG. 4 is a cross-sectional view of the aesthetic treatment device 10 taken along line A-A of FIG. 3;

DETAILED DESCRIPTION OF EMBODIMENTS

Figure 5:
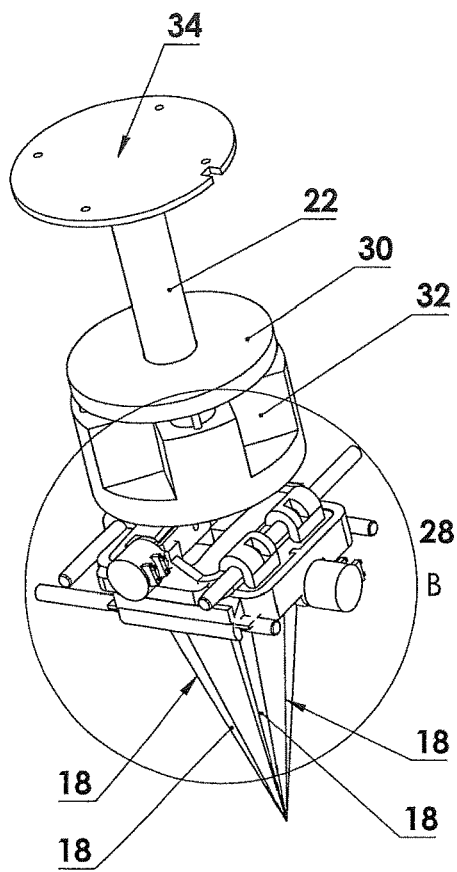
FIG. 5 is a perspective view of the internal parts of the aesthetic treatment device 10 shown in FIG. 1.

Reference will now be made in detail to the present embodiments of the present invention, examples of which are illustrated in the accompanying drawings, wherein like reference numerals refer to the like elements throughout. The embodiments are described below in order to explain the present invention by referring to the figures.

Aspects of the present invention disclose an aesthetic treatment device enabling application of focused light beams directly to skin hair or skin disorders, including miniature ones like hair follicles, stains, wrinkle lines, tattoo particles, miniature veins, etc., by treating the skin hair or disorder with minimal or no effect on the surrounding skin.

Aspects of the present invention disclose an aesthetic treatment device enabling recognition of areas of skin to be treated. Recognition of the disorder is performed by a dual illumination system and the application of coherent or noncoherent multiple focused light sources directly to a specific recognized target for aesthetic treatments.

Aspects of the present invention disclose a dual illumination system, such that an additional illumination system is provided in addition to a "regular" illumination system. The so called regular illumination system illuminates the skin from above and it is mounted around a camera lens. The configuration usually results in good illumination for the skin, but due to back reflections, hair and hair roots are not easily seen. The additional illumination system is mounted on a peripheral area of a system opening, and provides illumination on the area of the skin to be treated. (see US Patent Publ. No. 2013-0345685 to Aharon referred to later in this application) Features protruding out from the skin will be strongly illuminated while the skin will remain in relative darkness, creating an improved image emphasizing hair and outer surface features.

FIG. 1 is a side outside view of an assembled aesthetic treatment device 10 with a body 12 and an aperture 14 situated at one end thereof. According to an aspect, the body comprises a front cover 94 and a rear cover 96. FIG. 2 is a side perspective view of the aesthetic treatment device 10 showing the body 12 and the aperture 14. FIG. 3 is a front end view of the aesthetic treatment device 10 showing the aperture 14 with an opening 16, and light, such as laser beams 18. FIG. 4 is a cross-sectional view of the aesthetic treatment device 10 taken along line A-A of FIG. 3. Light sources (lasers) 20 emit light beams 18, and in the case the light sources are lasers, emit laser beams 18. A video camera 22 observes a surface region of skin 26 of a subject (not shown). Laser modules 24 power the lasers 20 and are mounted on an optical bench 32 to be parallel with the video camera 22. The laser modules 24 are mounted evenly distributed around a periphery of an optical bench 32, the optical bench 32 having a cylindrical outline. The lasers 20 may be 4, 6 or essentially any total in number, arranged about a center axis of the aesthetic treatment device 10. In the drawings, four (4) laser modules 24 are shown.

An optomechanical module 28 has two main tasks. First, the optomechanical module 28 focuses the lasers 20 to a single point (or points) designed to be below the surface region 26 and second, the optomechanical module 28 moves the focused laser beams 18 across the surface region 26 to any point within the video image area of the video camera 22, actually to any point just below the surface region 26.

FIG. 5 is a perspective view of the internal parts of the aesthetic treatment device 10 shown in FIG. 1, and includes the optomechanical module 28, the optical bench 32, and a camera base plate 34 on which the camera 22 is mounted. The camera 22 is inserted into an orifice 30 located and extending through the axis of the optical bench 32. The laser beams 18 are focused at the designed point even though they are coming in from different directions. Moreover, after passing a focal point, the laser beams 18 will diverge, and laser emission on an optical axis after the focal point will be zero. This feature is a very positive feature in relation to aspects of laser safety.

Figure 6:
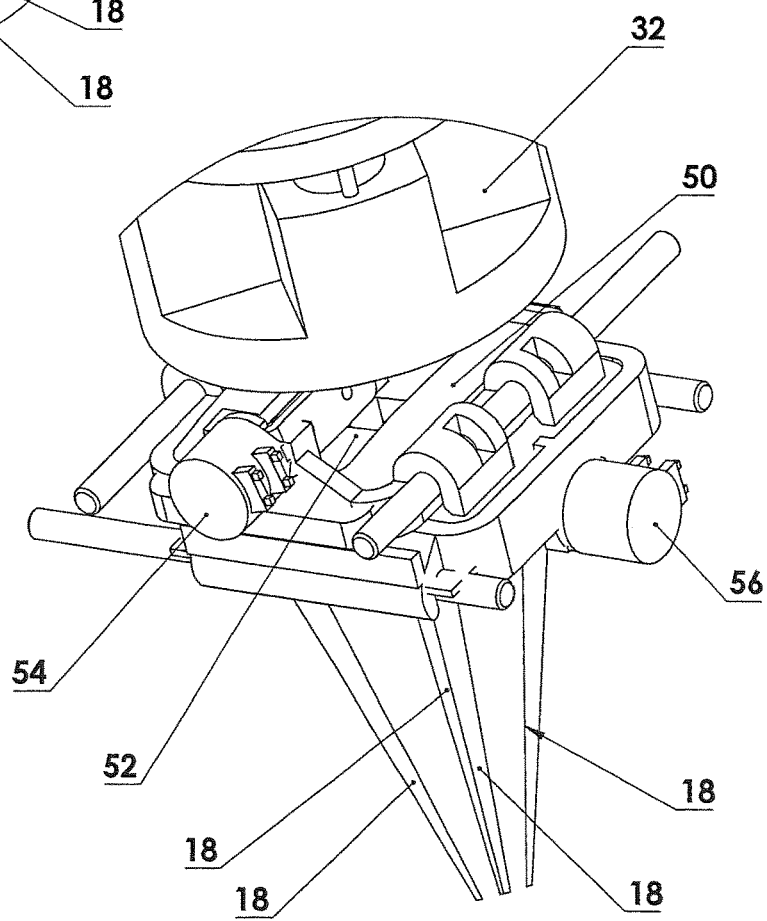
FIG. 6 is an exploded view of the optomechanical module 28 shown in FIG. 5.

FIG. 6 is an exploded view of the optomechanical module 28 shown in FIG. 5. The laser beams 18 pass through edge regions of first and second cylindrical optical elements (cylindrical lenses) 50 and 52. A cylindrical lens, in this example, has optical power in one direction, as opposed to a spherical lens that has optical power in all directions. The cylindrical optical elements 50 and 52 have optical power in only one direction, curvature on only one side, and their curvature resembles part of a cylinder. The cylindrical optical elements 50 and 52 are mounted in such a way that their optical power is orthogonal to each other. The curvature of the first, upper optical element 50 is on the downward side (see FIGS. 9-11), and the curvature of the second, lower optical element 52 is on the upward side (see FIGS. 9-11) facing the curvature of the cylindrical optical element 50. However, the order of the cylindrical optical elements 50, 52 may be switched in the direction from the camera 22 to the aperture 14 (see FIGS. 13A-14). The aesthetic treatment device 10 works with the cylindrical optical elements in either order (the order does not matter). The laser beams 18 passing through the first cylindrical optical element 50 will be focused in one direction and through the second cylindrical optical element 52 at an orthogonal direction. This will ensure proper focusing at the target where the laser beams 18 will be focused in both directions. The purpose of this arrangement is to allow steering of the focused laser beams 18 by two independent mechanical axes with no physical connection between optical carriages 84 and 86. This results in a greatly simplified system operation. Actual steering will be carried out by two orthogonal linear motors 54 and 56 which respectively drive the cylindrical optical elements 50 and 52. As noted above, the laser beams 18 pass through the edge regions of the cylindrical optical elements 50, 52.

Figure 7:
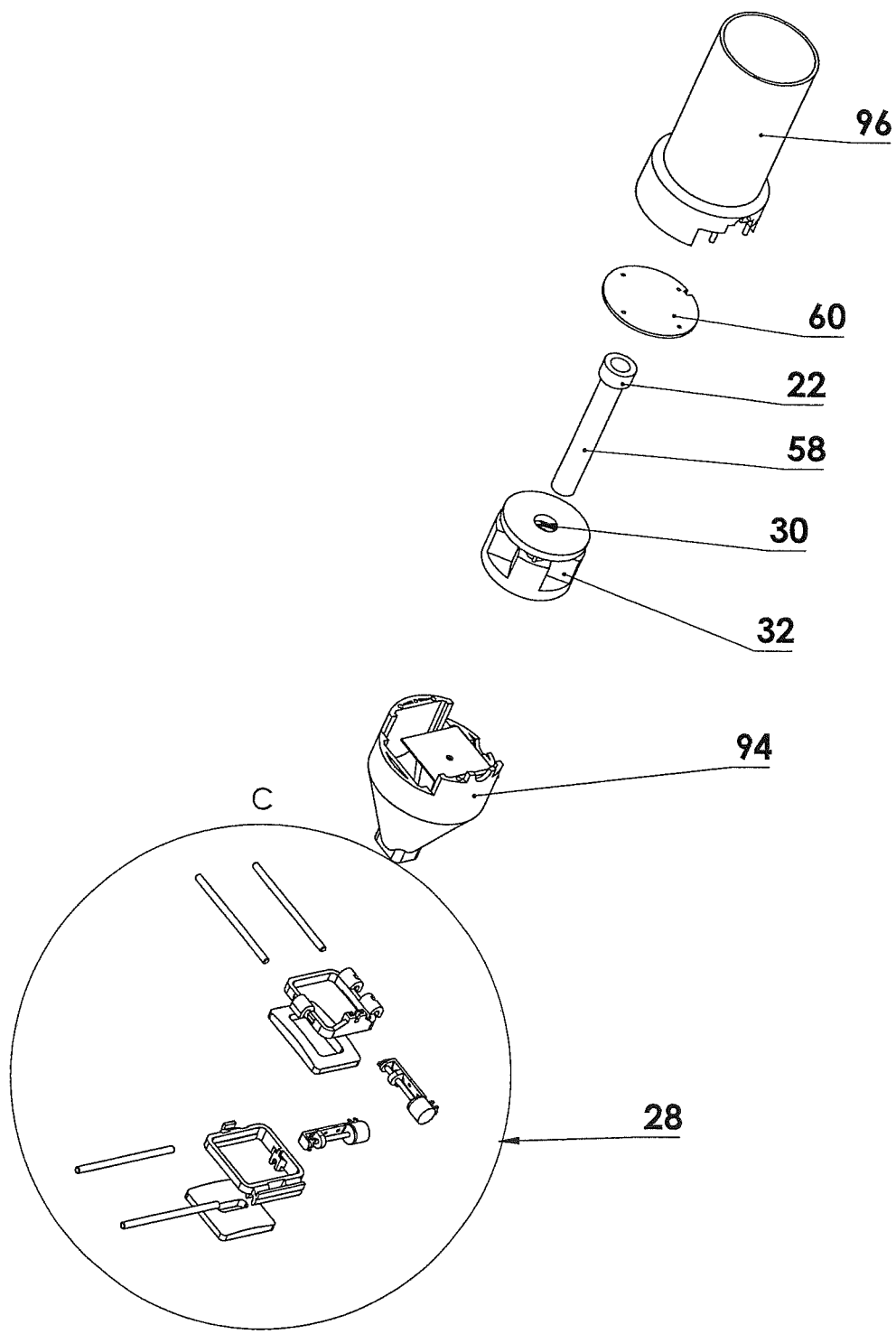
FIG. 7 is an exploded view of the aesthetic treatment device shown 1, including front and rear covers 94 and 96, optomechanical module 28, the laser modules 24, the video camera 22, camera optics 58, and CCD detector 60.
Figure 8:
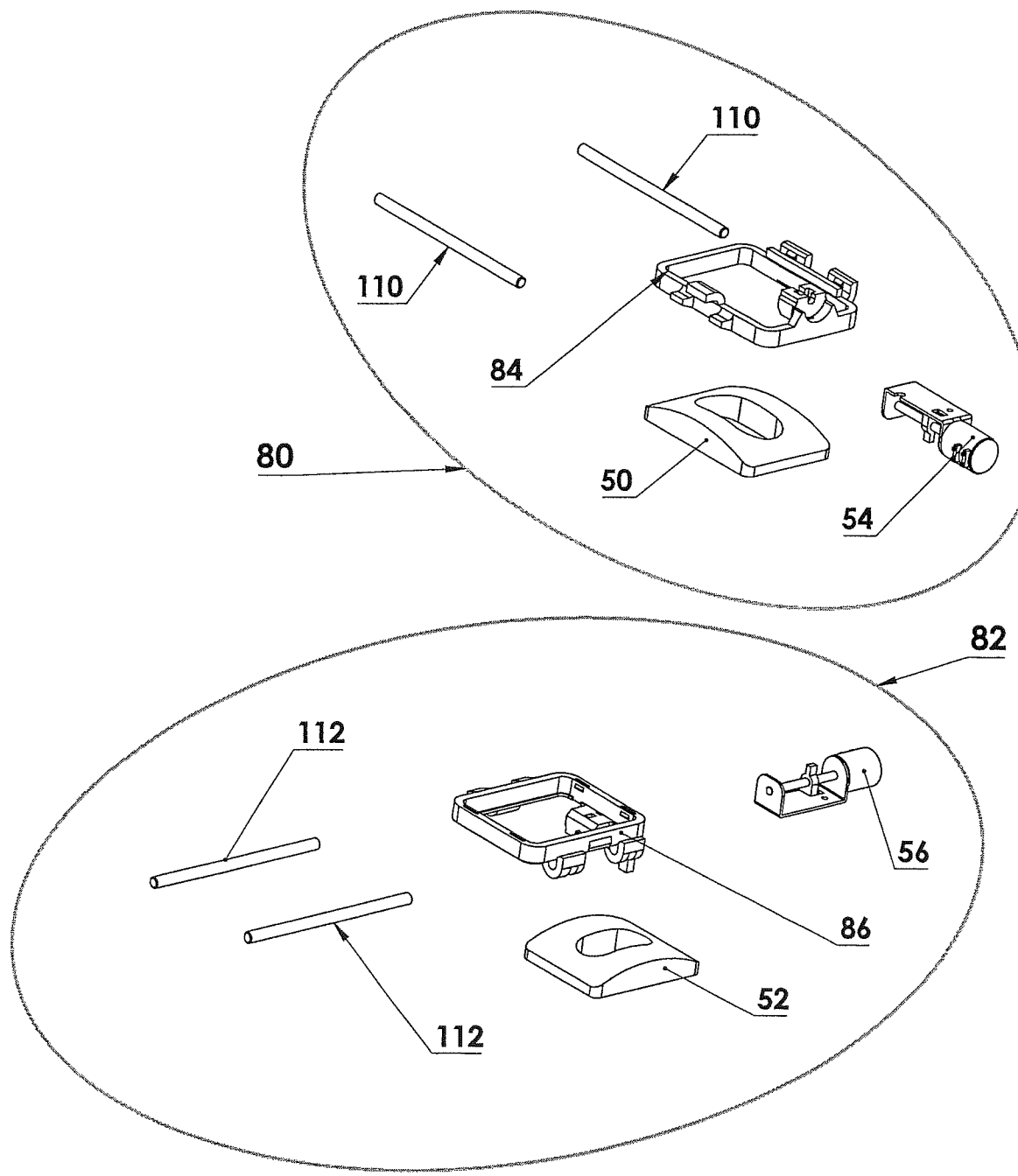
FIG. 8 is a blowout view of the optomechanical module of section C of FIG. 7.

FIG. 7 is an exploded view of the aesthetic treatment device 10, including front and rear covers 94 and 96, the optomechanical module 28, the laser modules 24, the video camera 22, camera optics 58, and a CCD detector 60. The camera optics 58 fit into the orifice 30 in the optical bench 32. FIG. 8 is a blowout view of the optomechanical module 28 of section C of FIG. 7. An x-axis mechanism shown as encircled elements 80 of the optomechanical module 28, controls movement of the laser beams 18 along an x-axis, and a y-axis mechanism, shown as encircled elements 82 of the optomechanical module 28, controls movement of the laser beams 18 along a y-axis orthogonal to the x-axis. Moving the optical elements 50 and 52, held by respective carriages 84 and 86, along their respective x and y—axes will move the laser beams 18 across an image plane of the video camera 22, and in this arrangement, the focal point of the laser beams 18 will move according to the amount of carriage movement in two dimensions. The carriage 84, driven by the motor 54, slides along first rails 110, and the carriage 86, driven by the motor 56, slides along second rails 112.

Figure 9:
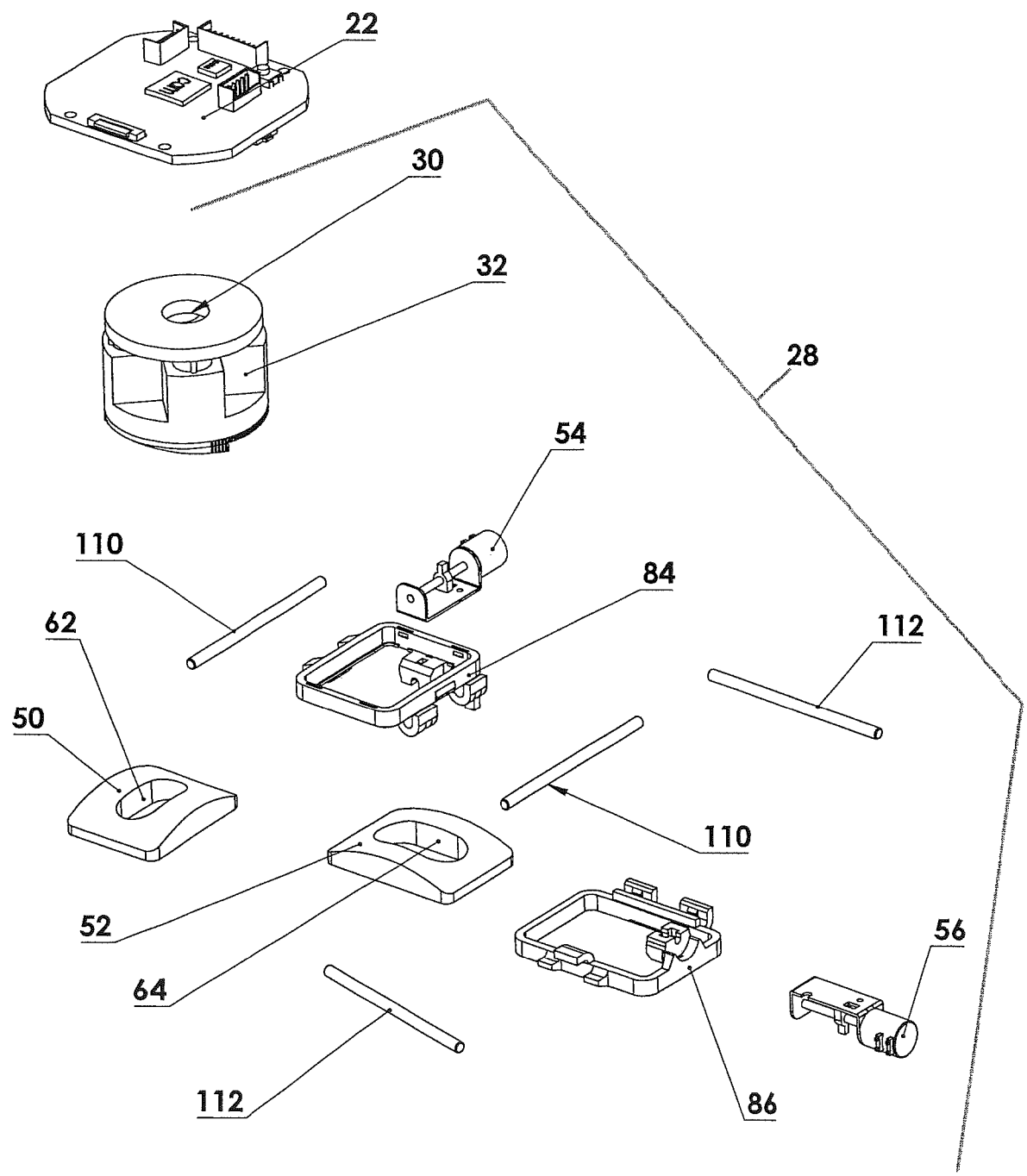
FIG. 9 is a more blownout view of the optomechanical module 28 of FIGS. 7 and 8.

FIG. 9 is a more blownout view of the optomechanical module 28 of FIGS. 7 and 8. As can be seen in FIG. 9, the bottom side of the cylindrical optical element 50 has a cylindrical shape with a rectangular shaped aperture 62 with its lengthwise direction being along the y-axis. The top side of the cylindrical optical element 52 (see FIG. 11) has a rectangular shaped aperture 64 with its lengthwise direction being along the x-axis, perpendicular to the y-axis direction.

In this embodiment, the cylindrical optical elements 50, 52 have the apertures 62 and 64 through which the video camera 22 can take a 2D image of the surface region 26 to detect hairs 120 or other treatment conditions on or above the surface of the skin.

Figure 10:
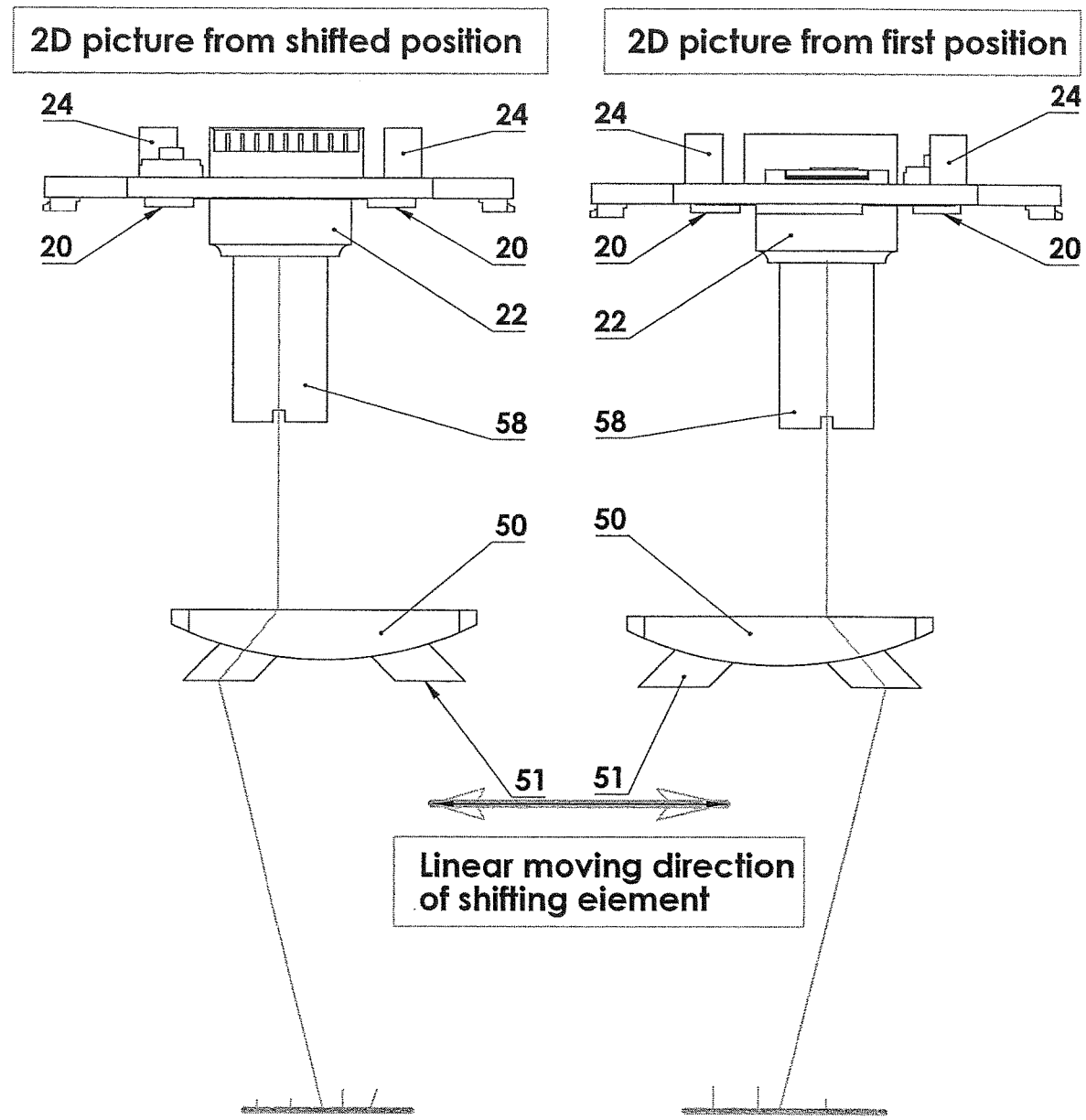
FIG. 10 is a cross-sectional view of the video camera, camera optics and the cylindrical optical elements, with the cylindrical optical elements in a first position and a shifted second position, of the aesthetic treatment device shown in FIG. 1.
Figure 11:
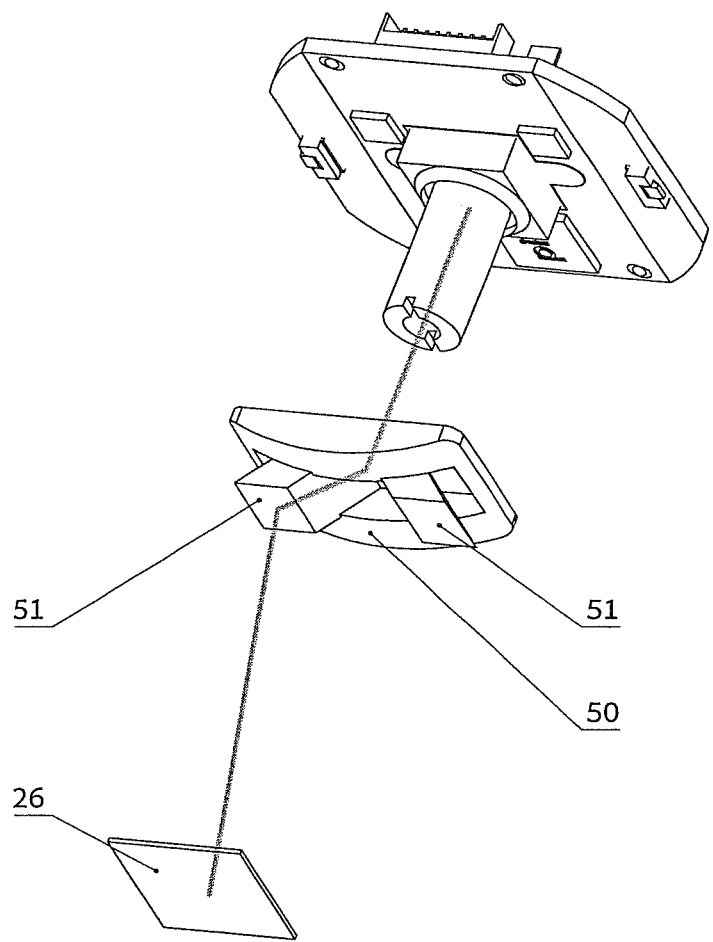
FIG. 11 shows a perspective view the elements shown in FIG. 10.

FIG. 10 is a cross-sectional view of the video camera 22, camera optics 58 and the cylindrical optical element 50, with the cylindrical optical element 50 in a first position and a shifted second position. FIG. 11 shows a perspective view of the cylindrical optical element 50 shown in FIG. 10. In this embodiment, the cylindrical optical element 50 has a cylindrical shape with a pair of rhomboids 51 in the location of the aperture 62. However, it is noted that instead of cylindrical optical element 50 having a pair of rhomboids, the cylindrical optical element 52 may instead have a pair of rhomboids 53 at the location of the aperture 64 (see FIG. 13A). Again, the order of the cylindrical optical elements 50, 52 does not matter.

Figure 12:
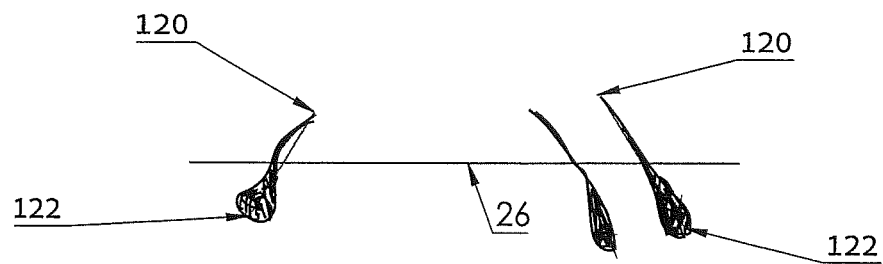
FIG. 12 shows a skin area which is searched for targets such as hairs and hair follicles.

The rhomboids 51 or 53 enable the ability of the video camera 22 to acquire a 3D image of the surface region 26. The optomechanical module 28 works like an eye, using parallax to determine the position of hairs or other skin conditions. The motors 54 and 56 have the cylindrical optical elements 50 and 52 in a first position to take an initial image of the surface region 26 to detect hairs 120, as shown in the right side drawing of FIG. 10, and shown in FIG. 12 as well. The initial image is viewed through the first of the two rhomboids 51 by the camera 22 and the aperture 64 of the second cylindrical optical element 52. The motor 54 then moves the cylindrical optical element 50 along its one axis, the y-axis, until the cylindrical optical element 50 is in the second position as shown in the left side drawing of FIG. 10, when the video camera 22 takes an additional image of the hairs 120. Here, the additional (second) image is viewed through the second of the two rhomboids by the camera 22 and the aperture 64.

It is possible that the aesthetic treatment device 10 also has one of the multi-illumination systems disclosed in U.S. Patent Publ. No. 2013-0345685 to Aharon to illuminate the hairs 120 that protrude from the skin surface to make them easier to see.

Later, during the operation to focus the laser beams 18 at hair follicles 122, the laser beams 18 pass through the lens parts of the cylindrical optical elements 50 and 52 along the y-axis, and the x-axis, respectively (and not the rhomboid part in this example), and based upon the positioning of the cylindrical optical elements 50 and 52, the lasers are focused under the skin at the determined positions of the hair follicles 122.

Figure 13A:
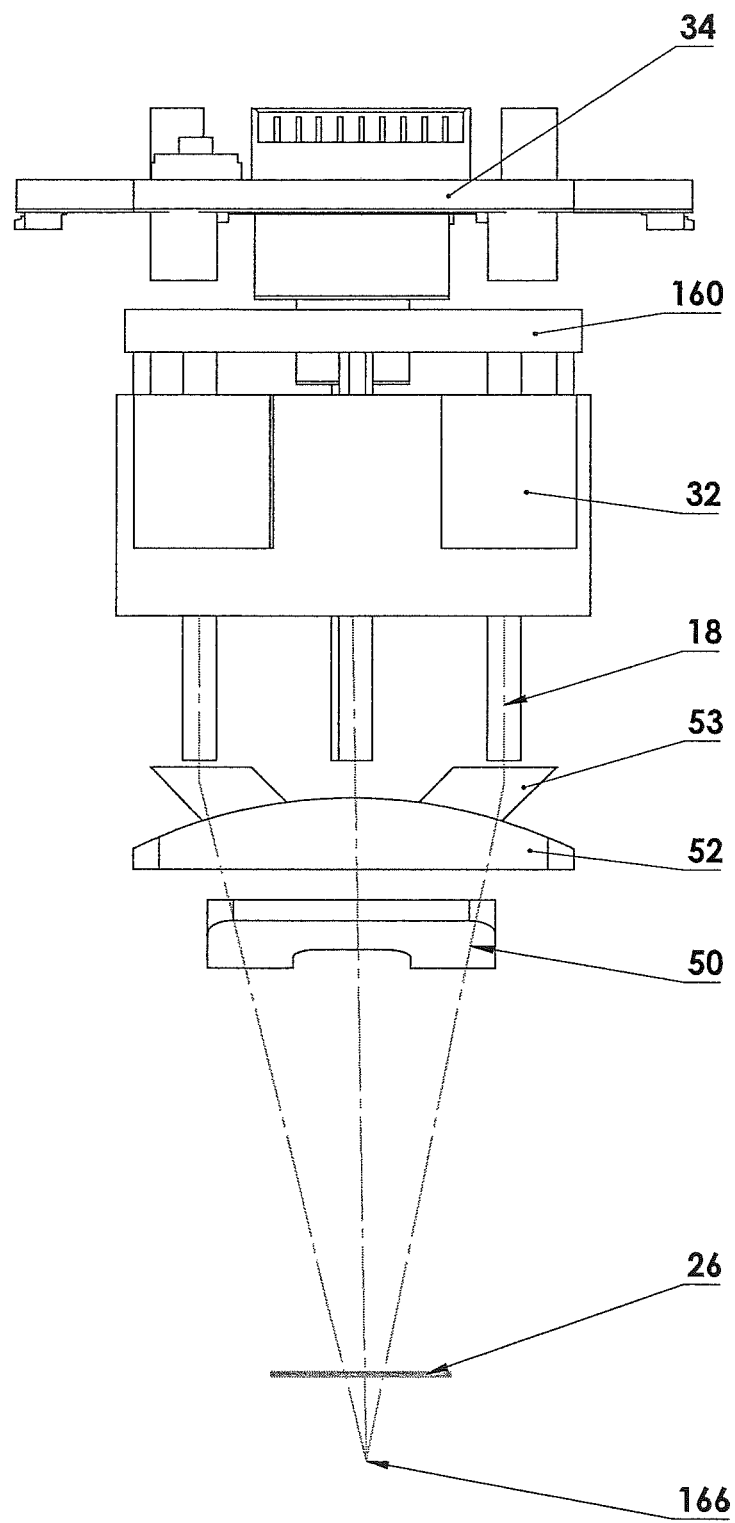
FIGS. 13A-13C are a plane view, a perspective view and a top view drawings illustrating the automatic search and treat system using four laser modules.
Figure 13B:
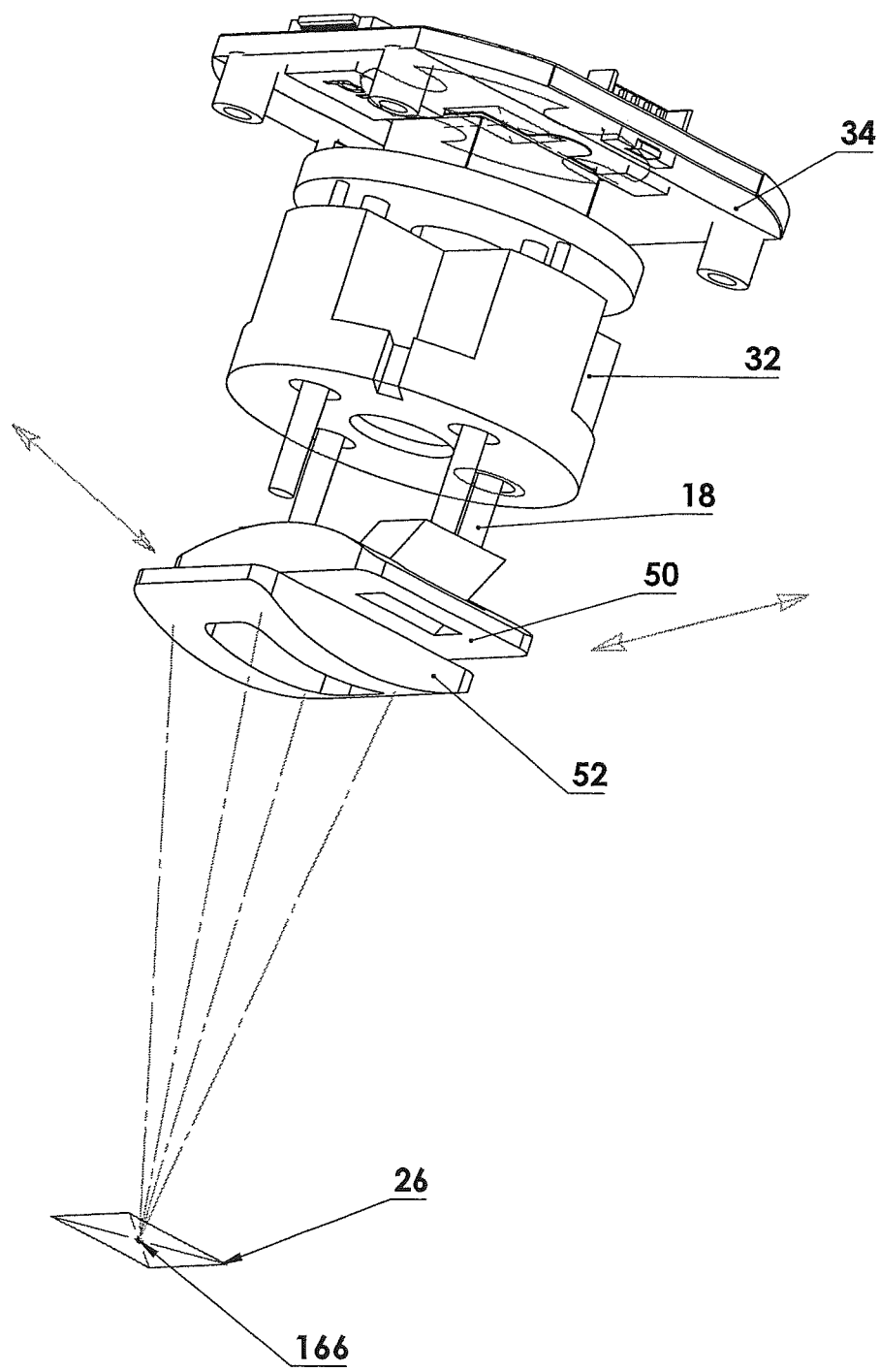
Figure 13:
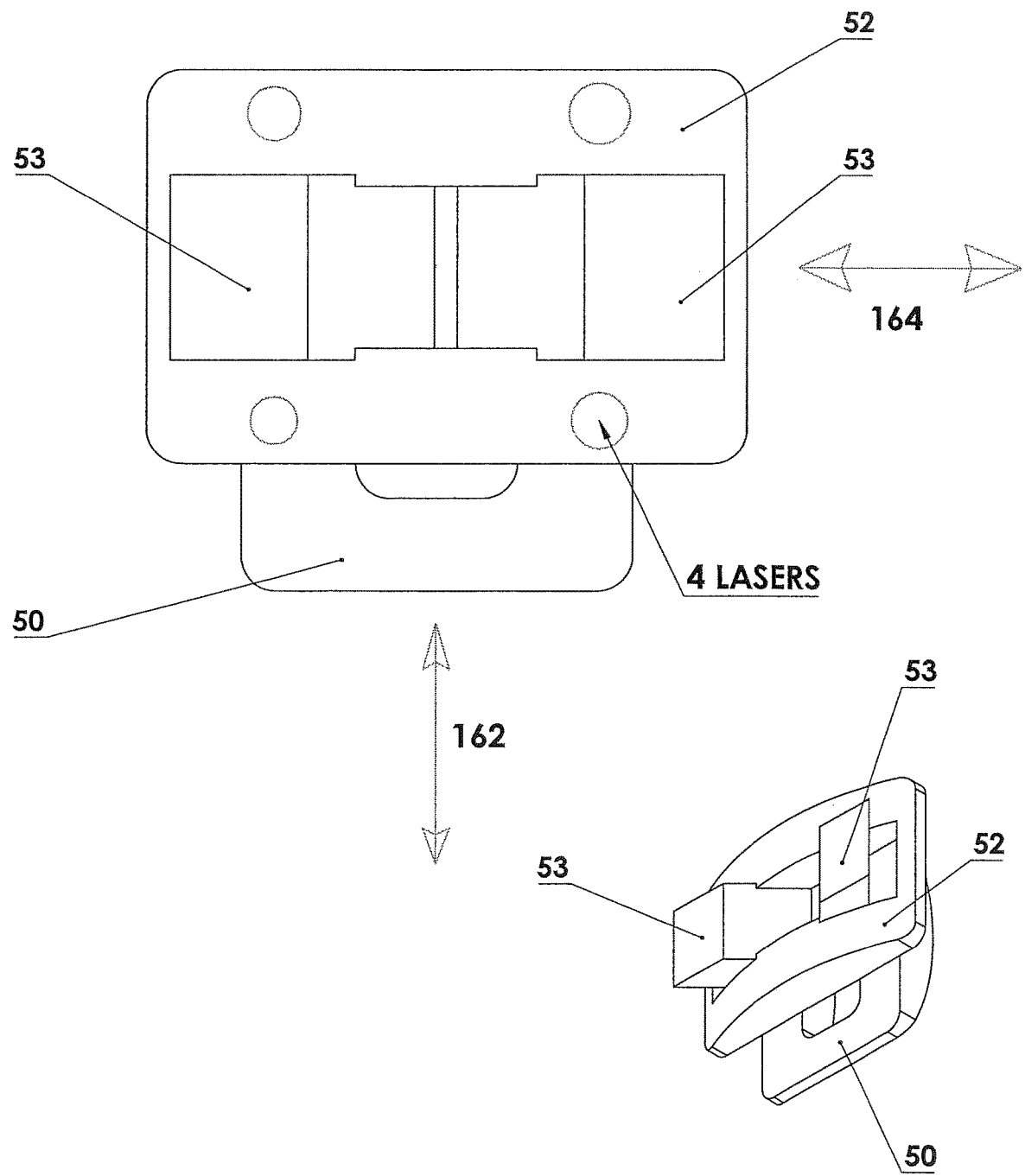

FIGS. 13A-13C are a plane view, a perspective view and a top view drawings illustrating the automatic search and treat system using the four laser modules 24. The rhomboids 53 are not shown in FIG. 13B for ease of view during this process.

FIG. 13A illustrates the propagation of four or more laser beams 18 which are in the or near the infrared region of the spectrum, i.e., shorter than 1800 nm and above 670 nm from the circular optical bench 32, and more specifically, in the 670-1000 nm range, a laser printed circuit board (PCB) 160 controls the lasers 20 of the laser modules 24 and the surface region of skin 26 is shown. The front and rear covers 94 and 96 are not shown (but see FIG. 1).

The laser beams 18 are focused by the cylindrical element 52 and cylindrical element 50, which perform focusing in perpendicular directions to each other through the cylindrical parts (not the rhomboid parts). The combination of the two cylindrical elements 50, 52 focuses all of the laser beams 18 to a point(s) located just beneath the treated surface region 26. Moving the cylindrical elements 50, 52 in first and second denoted directions 162 and 164 will scan the beams' focal point across the surface region 26 in two independent directions. The second cylindrical element 52 is equipped with two rhomboidal elements 53 that when shifted along a first denoted direction, allows imaging of the surface region 26 from two offset positions taken in 2D to create the 3D image using parallax as described above. FIG. 13C shows a top-down view with the focal point 166 of the laser beams 18.

Figure 14:
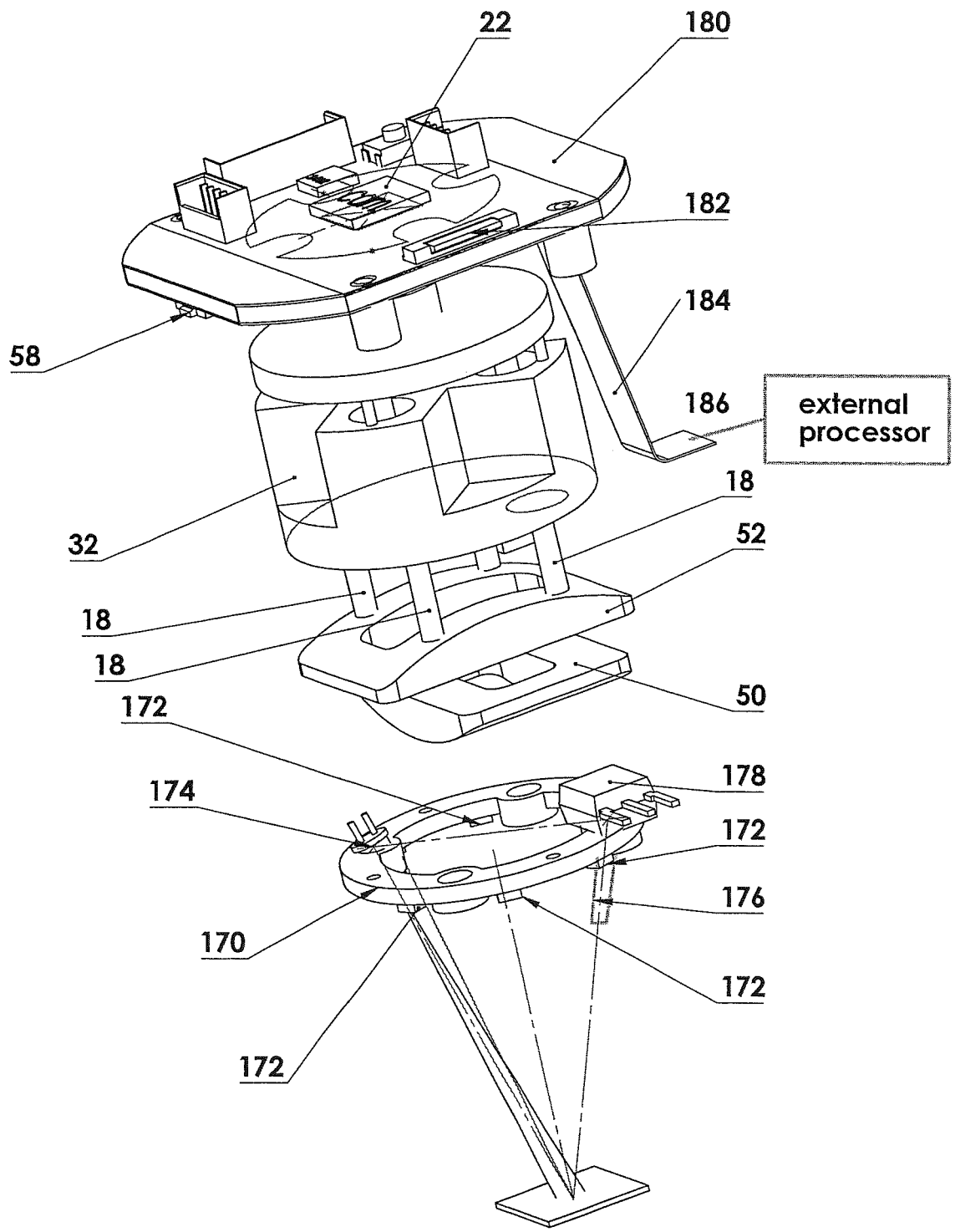
FIG. 14 shows a perspective exploded view of the aesthetic treatment device, including both the search mechanisms, the treatment mechanisms, and potential external processor.
Figure 16:
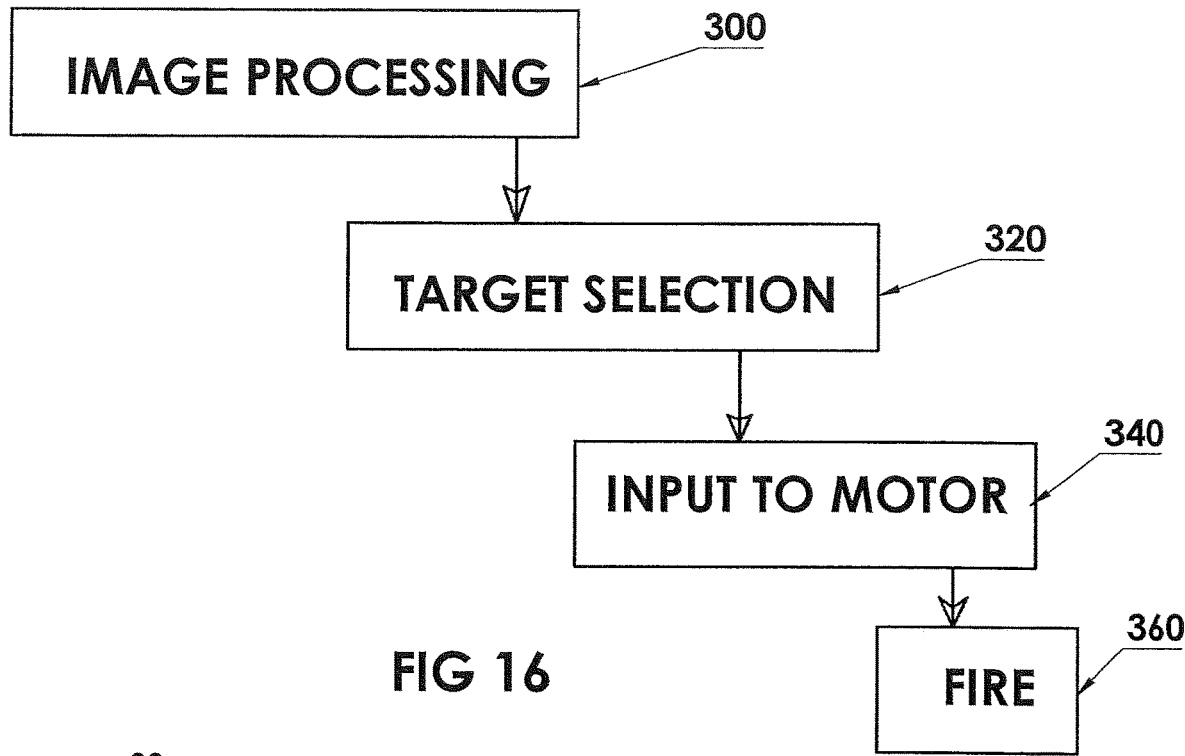
FIGS. 15-21 include the operation of the aesthetic treatment device shown in FIG. 1.
Figure 15:
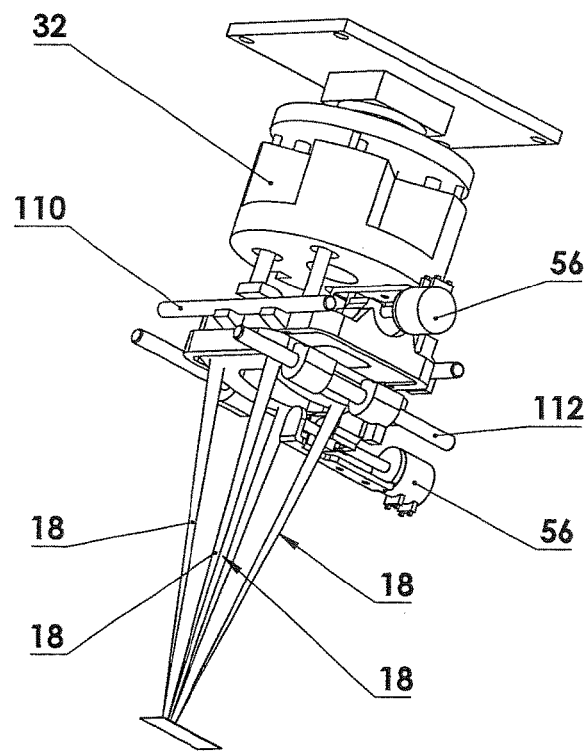
Figure 17:
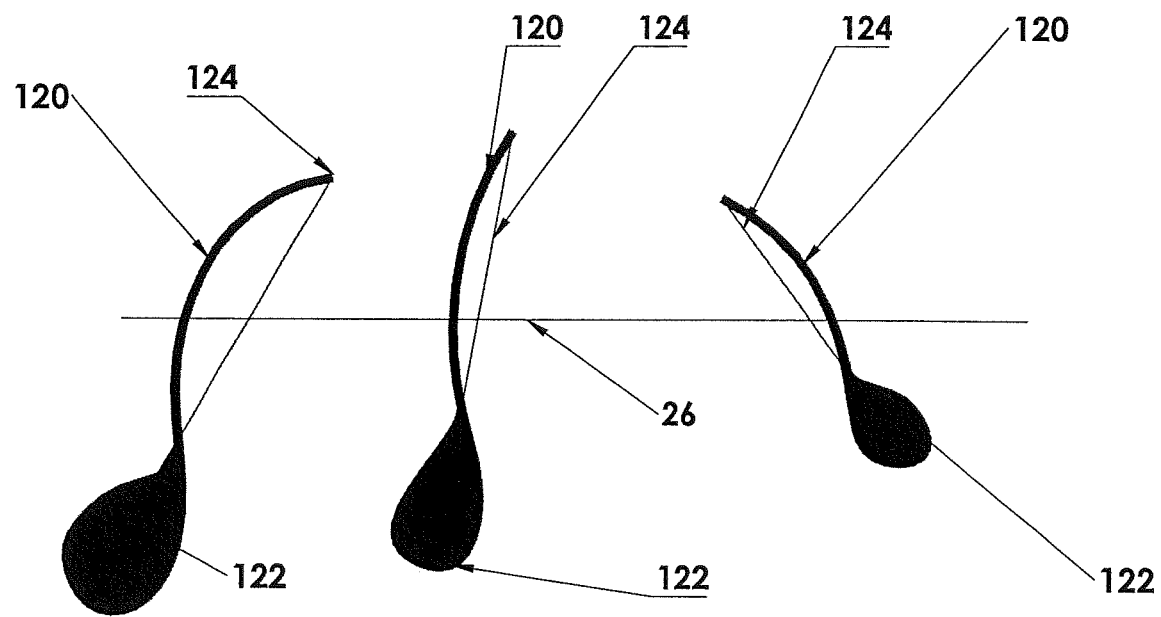

FIG. 14 shows the interior of the aesthetic treatment device 10 including both the detection elements and the treatment elements. A circular illumination printed circuit board (PCB) 170 is used to control light emitting diodes (LEDs) 172 (four are shown, but the number could vary) during the time that the video camera 22 is taking its images to search for the hairs 120, to then determine the location of the hair follicles 122. The LEDs 172 generally emit light in the visible range of about 400-700 nm. During this operation of seeking the locations of hair follicles 122 of the hairs 120, the video camera 22 is able to view through the apertures 62 and 64 the surface region of skin 26 and the hairs 120. An electro-optical proximity sensor comprises a specially designed light source 174, a hollow tube 176 and a light detector 178. The electro-optical proximity sensor detects if the aesthetic treatment device 10 is touching (or possibly immediately adjacent to) the surface region 26, depending upon whether the light emitted by the specially designed light source 174 travels through the hollow tube 176 and reaches the light detector 178, and is beneficial for safety reasons. The electro-optical proximity sensor may also be referred to as an electro-optical triangulation device. This sensor prevents accidental activation of the lasers 20 when the surface region 26 is not in the correct position near the aesthetic treatment device 10. When the surface region 26 is not touching or immediately adjacent to the electro-optical proximity sensor, the light from the light source 174 is not reflected by anything to travel back up through the hollow tube 176 to the light detector 178. Further, with separate light sources 20 for treatment and light sources 172 for illumination, there is no dependency at all between the illumination and treatment sources. As such, the light sources 20 and 172 may have the same wavelength or different wavelength depending upon the treatment application or the color of the surface region 26.

In FIG. 14, an electronic PCB 180, which is an electronic driver, has a connector 182 and/or possibly an extension/electric cord 184, which can be connected to any external processing element 186, like a processor, a computer, a mobile device like a cell phone or tablet, a lap top, etc. A processing element, such as a microcontroller, on the PCB 180 or, alternatively, the external processing element 186, contains the algorithms that will control the operation of the camera 22, the laser modules 24, the cylindrical lenses 50 and 52 and the LEDs 172. The location of the processor to control operations for detection and treatment, whether internal to the front and rear covers 94 and 96 of the aesthetic treatment device 10 or external, is not material to the present invention. The electronic PCB 180 controls driving of the laser modules 24 and the cylindrical lenses 50 and 52.

The operation of the aesthetic treatment device 10 is described with respect to FIGS. 15-21. Image processing is performed in operation 300, target selection is performed in operation 320, input to motors 54, 56 to direct the focal point 166 at the target is performed in operation 340, and firing of the lasers 20 is performed in operation 360.

Figure 18:
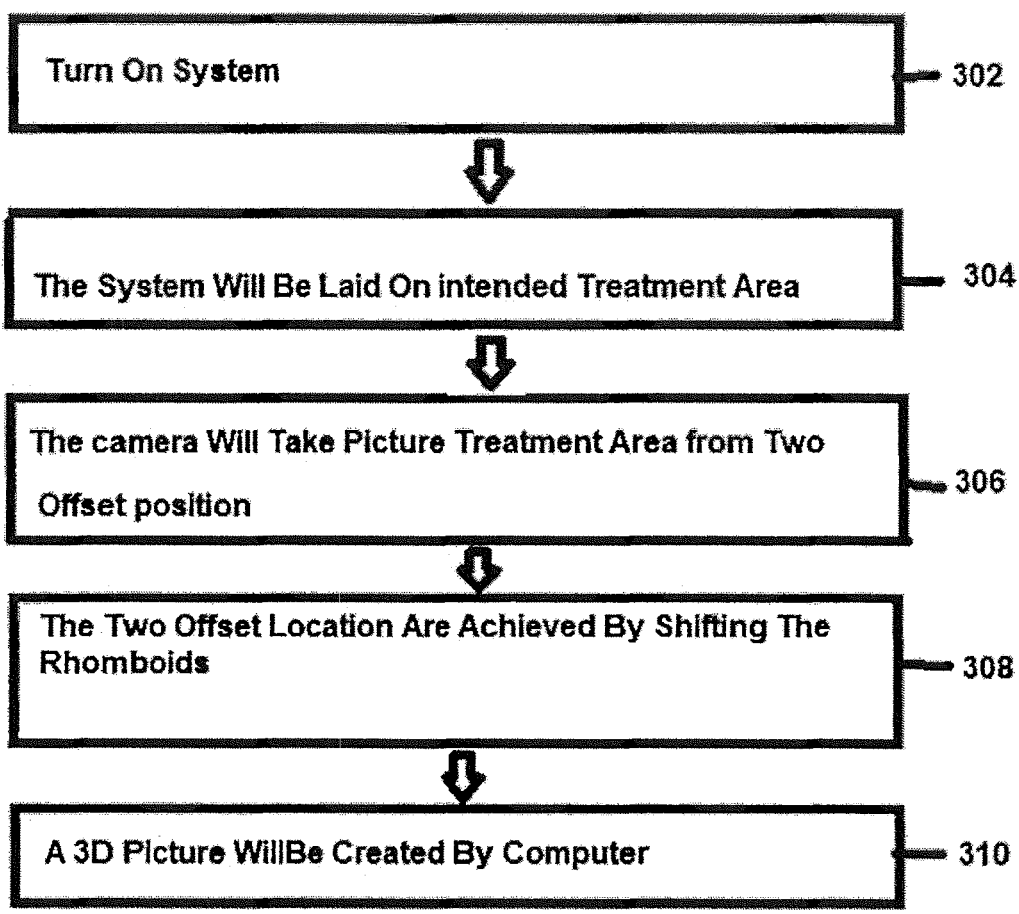

First, a description will be provided of the image processing operation 300 in FIG. 18. Initially, the aesthetic device 10 is turned on in operation 302. Then, the aperture 14 is placed over the surface region 26 in operation 304. It is possible that the surface region 26 penetrates somewhat into the aperture 14 upon the aperture 14 being pressed against the surface region 26. Then, the video camera 22 takes multiple images of the surface region 26 using the camera optics 58 and the camera 22, in other words, the camera 22 will take pictures of the surface region 26 from two offset positions, in operation 306. To do this, the cylindrical optical element 50 is arranged at a first position as shown in FIG. 10, right hand side through movement of the motor 54. The carriage 84 slides along the first rail 110 through the rotation of the motor 54 to be at the first position. An image of the surface region 26 is taken by having the video camera 22 view the surface region 26 through the first of the two rhomboids 51. Then, the motor 54 moves the cylindrical optical element 50 in a linear motion along the x-axis to the second position shown on the left side of FIG. 10. In each instance, the camera 22 views the surface region 26 through the rhomboids 51 of the cylindrical optical element 50 as set forth in operation 308. Hairs 120 will stick out of the surface region 26 at skin level. By taking two 2D images of the surface region 26 from multiple views due to the cylindrical optical element 50 being at the first and second positions at different times, two views of the surface region 26 are generated, and the processing element/processor either on the electronic PCB 180 within the body 12 or the external processing element 186 processor, which is external to the body 12, creates a 3-D image of the surface region 26, as per operation 310. As noted previously, it is possible to have a multi-illumination system propagate illumination light beams in free space across an orifice over the surface region and in a parallel direction to the surface region, whereby the hairs 120 standing up within the free space of the orifice and illuminated by the illumination light beams as proposed in U.S. Patent Pub. '685 to Aharon.

Figure 19:
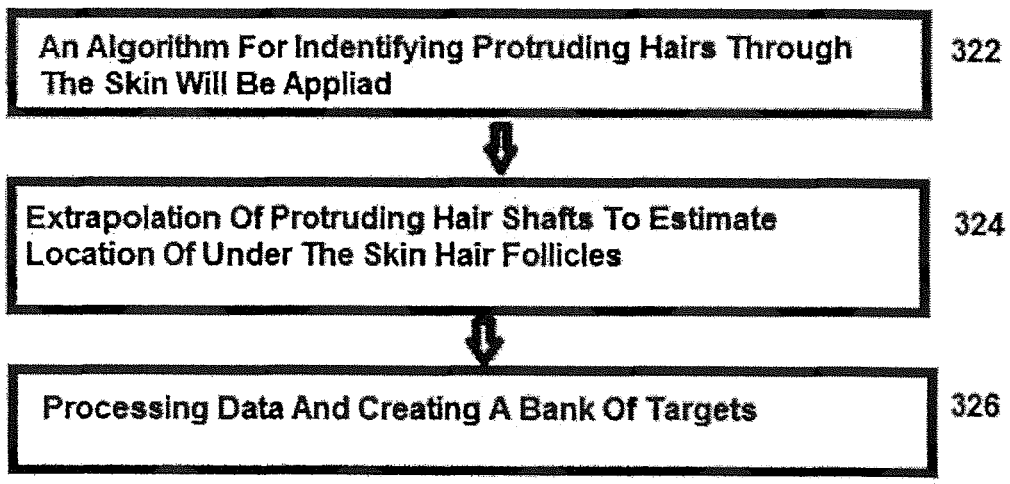

Now, the operation of target selection 320 will be explained in greater detail in FIG. 19. From the 3-D image, the processor or external processor 186 can construct the position and direction 124 of the hairs 120 using an algorithm based on parallax, similar to the operation of a human's (or any other animal's) eyes, as per operation 322. The processor or external processor 186 assumes that a hair follicle is 2-3 mm under skin level, so that the positions of the hair follicles 122 can be determined underneath the skin, using extrapolation of the location and angle of the protruding hair 120 to estimate the location under the surface region 26 that the hair follicles 122 are actually located, as per operation 324. This location of the hair follicles 122 is part of the target selection process 320. This depth is based upon biology, but is adjustable in the aesthetic treatment device 10 depending upon the specific situation, subject and the type of procedure that is to be performed by the laser beams 18. The process is repeated in operation 326 over the surface region 26, the processor or external processor 186 processes the location data for a number of targets within the surface region 26, and creates a bank of the targets (hair follicles 122, for example), in preparation of treatment.

Thus, the aesthetic treatment device 10 now knows the positions of the hair follicles 122, thus automatically determining the positions of the hair follicles 122 without the user of the aesthetic treatment device 10 having to manually direct the laser beams 18 towards hair follicles 122. The locations of the hair follicles 122 do not need to be very accurate as the laser beam focal point is larger as compared to the hair follicles 122.

Alternatively, to determine hair follicle 126 position, instead of using an algorithm based on parallax by using two images taken by the video camera 22 to generate a 3D model, it is possible to set up the aesthetic device 10 to have the video camera 22 take one image of the surface region 26 to try to find the hairs 120 and hair follicles 126 within the surface region 26, and if successful, the taking of a second image and using parallax to determine the hair 120 and hair follicles 126 is skipped. If not successful, then the cylindrical element 50 is moved to the second position, a second image is taken, and the algorithm using parallax is performed to determine the location of the hairs 120 and hair follicles.

Figure 20:
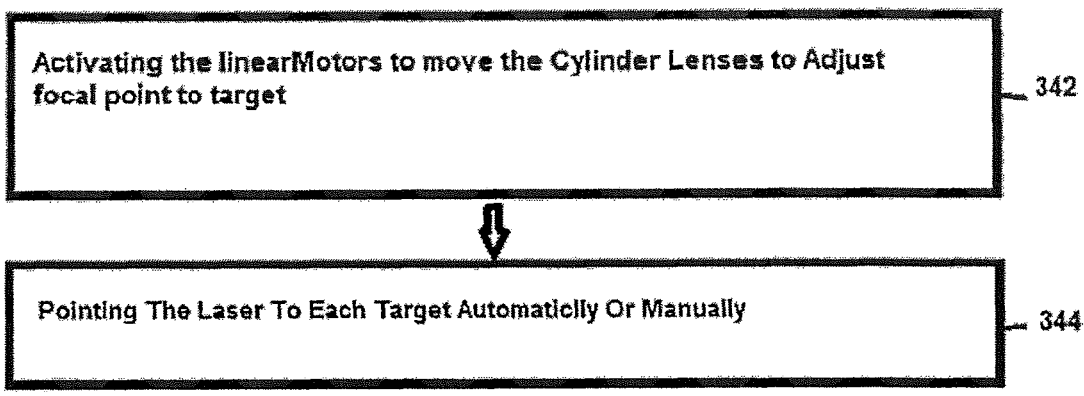

The operation 340 is explained in greater detail as shown in FIG. 20. The optical elements 50 and 52 are moved so that the laser beams 18 pass through the cylindrical (curved) portions of the optical elements 50 and 52 so as to direct the laser beams 18 toward a first hair follicle 122, then to a position to direct the laser beams 18 toward a second hair follicle 122, and so on.

More specifically, in operation 342, the processor on the electronic PCB 180 or the external processor 186, in response to knowing where the hair follicles 122 are located, activates (controls) the motors 54 and 56, as shown in the input to motor process 340, to move the carriages 84 and 86 along the first and second rails 110 and 112, so as to move the cylindrical optical elements 50 and 52 in the x-axis and y-axis directions, wherein the focal point 166 of the laser beams 18 is moved around the surface region 26 to the various locations just underneath the skin area 26 where the hair follicles 122 have been calculated to be located (see operation 344). During this process, the multiple laser beams 18 are focused by the cylindrical optical elements 50 and 52, creating multiple footprints on the skin surface where the different laser beams first contact the skin of the patient. Consequently, it is more possible to diffuse the laser power of the laser beams 18 than by focusing all of them on one spot of the skin surface, thereby causing less damage while still providing treatment under the skin. Alternatively, to automatically point the laser beams 18 to each target hair follicle 122, it is possible to set the aesthetic device in a manual mode, where the user can manually move the laser beam 18 focal point 166.

Figure 21:
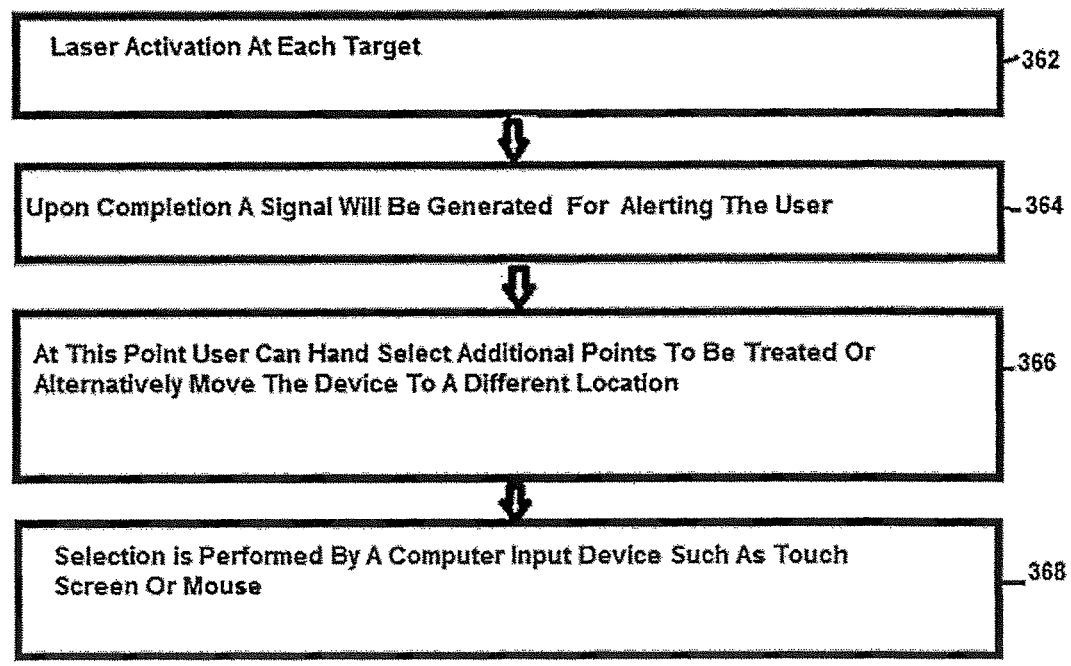

Now, the fire process 360 will be described in greater detail as shown in FIG. 21. The processor or external processor 186 instructs the laser modules 24 to emit the laser beams 18 through the cylindrical optical elements 50 and 52, in a fire process 362, so that the cylindrical optical elements 50 and 52 direct the laser beams 18 to be under the surface region 26 at a depth under the skin, such as 2-3 mm, and at the location of the first hair follicle 122 and then to the next hair follicle 122 to be fired upon, and so on, until all of the hair follicles in the surface region 26 have been fired upon. Upon completion of the firing of the lasers 20 at the hair follicles 122 within the surface region 26, a signal will be generated to alert the user that the firing process has been completed, see operation 364. At this point, the user can hand select additional points of the surface region 26 to be treated or, alternatively, can move the aesthetic treatment device to a new, next location for searching. The actual selection can be performed on any input device, such as a touch screen, a mouse, touchpad, etc., per operation 368.

Figure 23:
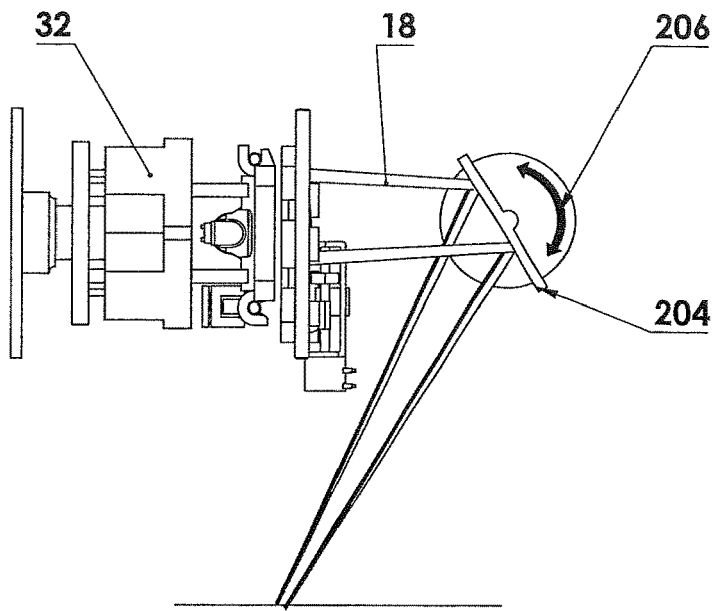
FIG. 22 shows a perspective view of an interior of an aesthetic treatment device according to another aspect and FIG. 23 shows a side view of the aesthetic treatment device of FIG. 22.
Figure 22:
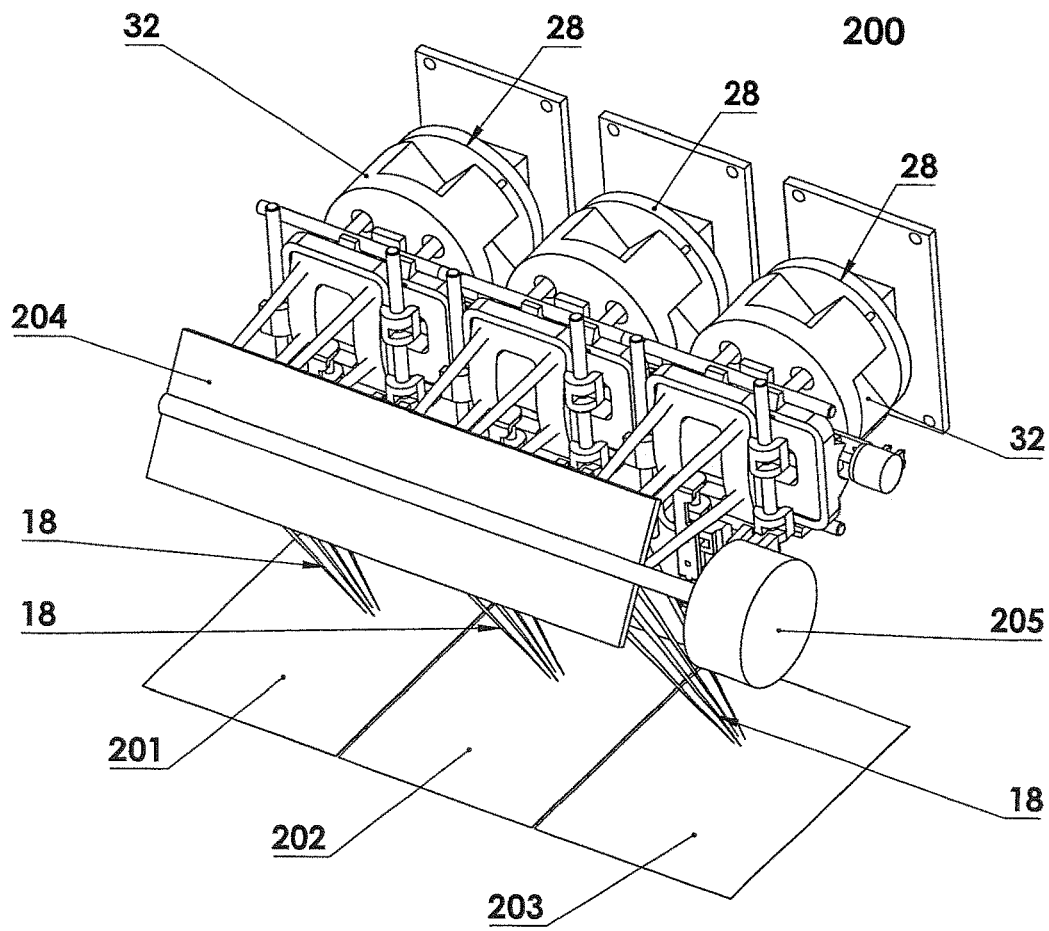

FIG. 22 shows a perspective view of an interior of an aesthetic treatment device 200 according to another embodiment. FIG. 23 shows a side view of the interior of the aesthetic treatment device 200. In this embodiment, there are three optomechanical modules 28 as shown in FIGS. 1-11 which are coupled together, parallel to each other and arranged in a row to enable the scanning and treatment of a larger region of skin simultaneously, and in a shorter amount of time. Of course, two, four or more optomechanical modules 28 may be provided. A mirror 204, rotated by a motor 205, reflects images of three surface regions 201-203 back towards three (3) corresponding video cameras 22 in a process as described previously with respect to FIG. 10. An arrow 206 shows the mirror's 204 rotation directions initiated by the motor 205. The surface regions 201, 202 and 203 are scanned in one direction by the mirror 204, which reflects the three sets of laser beams 18 from the three respective optomechanical modules 28, so that the regions of skin 201, 202 and 203 will be simultaneously or serially treated by the three parallel optomechanical modules 28 through movement of the cylindrical optical elements 50, 52 associated with each optomechanical module 28 to fire each hair follicle 122 found in each of the three regions of skin 201, 202 and 203.

In this embodiment, the motor 205 rotates so as to rotate the mirror 204 about an optical axis perpendicular to the optical axes of the three optomechanical modules 28, thereby enabling the three video cameras 22 to view three new surface regions 201-203 which are linearly placed in a direction perpendicular to the optical axis of the mirror 204 and the search and firing procedures are repeated. In this way, instead of searching only 1 surface region 26 at a time, multiple surface regions 201, 202 and 203 can be searched and fired upon, and then a plurality of next surface regions 201, 202 and 203 can be search and fired upon automatically through the rotation of the mirror 204, thereby potentially significantly enhancing the speed at which a large region of skin (made up of many surface regions) of a patient may be treated.

Thus, based on the foregoing, aspects of this invention relate generally to an aesthetic treatment device and method to automatically detect targets such as hairs and hair follicles within a small area of skin enclosed by an aperture of the aesthetic treatment device, and to automatically direct light sources (laser beams) on the specific area (on or under the skin) without affecting, and damaging the surrounding skin area.

Although a few embodiments of the present invention have been shown and described, it would be appreciated by those skilled in the art that changes may be made in this embodiment without departing from the principles and spirit of the invention, the scope of which is defined in the claims and their equivalents.

The invention claimed is:

1. An aesthetic treatment device for treatment of a predetermined surface region of skin by contacting a surface of the skin, the aesthetic treatment device comprising:
    an optical bench with an imaging device;
    multiple treatment laser modules configured to emit laser beams having different wavelengths, and mounted on a perimeter of the optical bench;
    a mechanical device configured to lie on the predetermined area of skin during the treatment and having an orifice to enable the multiple laser beams to have focal points under the skin along a focal axis;
    first and second cylindrical lenses which are independently movable in perpendicular directions substantially perpendicular to the predetermined area of skin, to move a focus and convergence of the multiple laser beams throughout the surface region of the skin based upon the operations in the perpendicular direction, creating the focal points under the surface region of the skin; and
    wherein the imaging device is a camera and configured to discern features on or under the surface region of the skin;
    wherein the first and second cylindrical lenses are configured to move to direct the focal points to treatment targets related to the discerned features;
    wherein the first cylindrical lens have first and second rhomboids protruding from a curved surface;
    wherein the camera is configured to take a first image of the surface region as viewed through the first rhomboid when the first cylindrical lens is at a first position and configured to take a second image of the surface region as viewed through the second rhomboid when the first cylindrical lens has moved along one of the perpendicular directions to a second different position;
    wherein the first and second images are configured to generate a 3-dimensional image, to recognize a feature to be treated within the surface region.

2. The aesthetic treatment device according to claim 1, further comprising:
    an electro-optical triangulation device configured to remotely sense whether the surface region is at the orifice of the mechanical device, and control activation of the laser modules according to the sensing of the surface region at the orifice of the mechanical device.

* * * * *